United States Patent
Buffa et al.

(10) Patent No.: US 10,023,658 B2
(45) Date of Patent: Jul. 17, 2018

(54) CONJUGATES OF OLIGOMER OF HYALURONIC ACID OR OF A SALT THEREOF, METHOD OF PREPARATION THEREOF AND USE THEREOF

(71) Applicant: Contipro a.s., Dolni Dobrouc (CZ)

(72) Inventors: Radovan Buffa, Humenne (SK); Ivana Basarabova, Medzilaborce (SK); Kristina Nesporova, Brno (CZ); Tereza Ehlova, Dobruska (CZ); Ondrej Kotland, Predmerice nad Labem (CZ); Petra Sedova, Ceska Trebova (CZ); Leos Hromek, Medlesice (CZ); Vladimir Velebny, Zamberk (CZ)

(73) Assignee: Contipro a.s., Dolni Dobrouc (CZ)

( * ) Notice: Subject to any disclaimer, the term of this patent is extended or adjusted under 35 U.S.C. 154(b) by 0 days.

(21) Appl. No.: 15/124,827

(22) PCT Filed: Mar. 10, 2015

(86) PCT No.: PCT/CZ2015/000018
§ 371 (c)(1),
(2) Date: Sep. 9, 2016

(87) PCT Pub. No.: WO2015/135511
PCT Pub. Date: Sep. 17, 2015

(65) Prior Publication Data
US 2017/0015759 A1    Jan. 19, 2017

(30) Foreign Application Priority Data
Mar. 11, 2014  (CZ) .................................... 2014-150

(51) Int. Cl.
*C08B 37/08*   (2006.01)
*A61K 31/728*  (2006.01)
*A61K 47/61*   (2017.01)

(52) U.S. Cl.
CPC ........ *C08B 37/0072* (2013.01); *A61K 31/728* (2013.01); *A61K 47/61* (2017.08)

(58) Field of Classification Search
None
See application file for complete search history.

(56) References Cited

U.S. PATENT DOCUMENTS

| | | |
|---|---|---|
| 3,720,662 A | 3/1973 | Tessler et al. |
| 3,728,223 A | 4/1973 | Kaneko et al. |
| 4,043,331 A | 8/1977 | Martin et al. |
| 4,205,025 A | 5/1980 | Hart et al. |

(Continued)

FOREIGN PATENT DOCUMENTS

| | | |
|---|---|---|
| CA | 2512730 A1 | 7/2004 |
| CH | 628088 A5 | 2/1982 |

(Continued)

OTHER PUBLICATIONS

Jou, Chi-Hsiung et al., "Biocompatibility and Antibacterial Activity of Chitosan and Hyaluronic Acid Immobilized Polyester Fibers," Journal of Applied Polymer Science vol. 104, No. 1, 2007, pp. 220-225.

(Continued)

*Primary Examiner* — Layla D Berry
(74) *Attorney, Agent, or Firm* — Wood Herron & Evans LLP

(57) ABSTRACT

The invention relates to conjugates of hyaluronic acid oligomer according to the general formulae I, II III or IV, or a salt thereof, the method of preparation thereof and use thereof, where the oligomer is bonded to the respective substrate by its ending anomeric center via a bi-functional amino linker by means of an amino or imino bond. This type of conjugates allows releasing oligomers in their native form. The prepared systems exhibited an enhanced biological activity against selected lines of cancer cells.

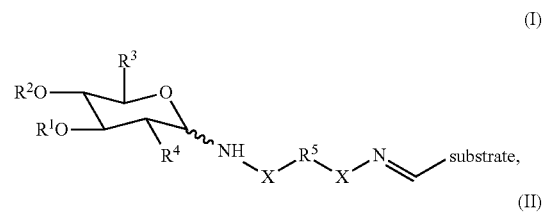

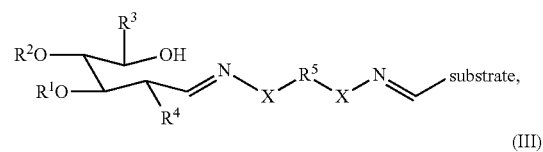

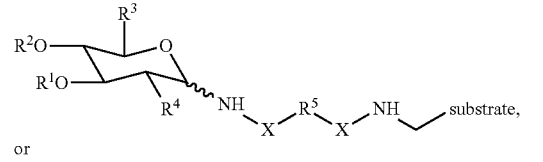

or

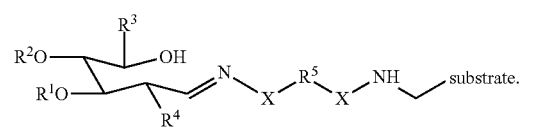

19 Claims, 1 Drawing Sheet

(56) References Cited

U.S. PATENT DOCUMENTS

| | | |
|---|---|---|
| 4,258,134 A | 3/1981 | Yoshida et al. |
| 4,713,448 A | 12/1987 | Balazs et al. |
| 4,761,401 A | 8/1988 | Couchman et al. |
| 4,851,521 A | 7/1989 | Della Valle et al. |
| 4,965,353 A | 10/1990 | Della Valle et al. |
| 5,455,349 A | 10/1995 | Grasshoff et al. |
| 5,462,976 A | 10/1995 | Matsuda et al. |
| 5,520,916 A | 5/1996 | Dorigatti et al. |
| 5,522,879 A | 6/1996 | Scopelianos |
| 5,550,225 A | 8/1996 | Philippe |
| 5,616,568 A | 4/1997 | Pouyani et al. |
| 5,658,582 A | 8/1997 | Dorigatti et al. |
| 5,676,964 A | 10/1997 | Della Valle et al. |
| 5,690,961 A | 11/1997 | Nguyen |
| 5,824,335 A | 10/1998 | Dorigatti et al. |
| 5,868,973 A | 2/1999 | Muller et al. |
| 6,025,444 A | 2/2000 | Waki et al. |
| 6,075,066 A | 6/2000 | Matsuda et al. |
| 6,207,134 B1 | 3/2001 | Fahlvik et al. |
| 6,288,043 B1 | 9/2001 | Spiro et al. |
| 6,509,039 B1 | 1/2003 | Nies |
| 6,613,897 B1 | 9/2003 | Yatsuka et al. |
| 6,632,802 B2 | 10/2003 | Bellini et al. |
| 6,673,919 B2 | 1/2004 | Yui et al. |
| 6,683,064 B2 | 1/2004 | Thompson et al. |
| 6,719,986 B1 | 4/2004 | Wohlrab et al. |
| 6,902,548 B1 | 6/2005 | Schuler et al. |
| 6,953,784 B2 | 10/2005 | Thompson et al. |
| 7,125,860 B1 | 10/2006 | Renier et al. |
| 7,214,759 B2 | 5/2007 | Pacetti et al. |
| 7,550,136 B2 | 6/2009 | Warner et al. |
| 7,680,038 B1 | 3/2010 | Gourlay |
| 7,951,936 B2 | 5/2011 | Sato |
| 8,247,546 B2 | 8/2012 | Stucchi et al. |
| 9,017,725 B2 | 4/2015 | Mitra et al. |
| 2002/0026039 A1 | 2/2002 | Bellini et al. |
| 2002/0076810 A1 | 6/2002 | Radice et al. |
| 2003/0163073 A1 | 8/2003 | Effing et al. |
| 2003/0205839 A1 | 11/2003 | Bachrach |
| 2004/0101546 A1 | 5/2004 | Gorman et al. |
| 2004/0192643 A1 | 9/2004 | Pressato et al. |
| 2005/0112349 A1 | 5/2005 | Laurencin et al. |
| 2005/0119219 A1 | 6/2005 | Bellini et al. |
| 2005/0126338 A1 | 6/2005 | Yadav |
| 2005/0266546 A1 | 12/2005 | Warner et al. |
| 2006/0046590 A1 | 3/2006 | Chu et al. |
| 2006/0084759 A1 | 4/2006 | Calabro et al. |
| 2006/0188578 A1 | 8/2006 | Fernandez et al. |
| 2006/0189516 A1 | 8/2006 | Yang et al. |
| 2006/0281912 A1 | 12/2006 | James et al. |
| 2007/0149441 A1 | 6/2007 | Aeschlimann et al. |
| 2007/0202084 A1 | 8/2007 | Sadozai et al. |
| 2008/0063617 A1 | 3/2008 | Abrahams et al. |
| 2008/0071001 A1 | 3/2008 | Sato |
| 2008/0124395 A1 | 5/2008 | Chen et al. |
| 2009/0024019 A1 | 1/2009 | Stein et al. |
| 2009/0180966 A1 | 7/2009 | Borbely et al. |
| 2009/0252810 A1 | 10/2009 | Tommeraas et al. |
| 2010/0002155 A1 | 1/2010 | Yamaguchi et al. |
| 2010/0172892 A1 | 7/2010 | Uvarkina et al. |
| 2010/0247908 A1 | 9/2010 | Velev et al. |
| 2010/0310631 A1 | 12/2010 | Domard et al. |
| 2010/0310853 A1 | 12/2010 | Schwiegk et al. |
| 2010/0316682 A1 | 12/2010 | Chen et al. |
| 2011/0020917 A1 | 1/2011 | Wen et al. |
| 2011/0111012 A1 | 5/2011 | Pepper et al. |
| 2011/0200676 A1 | 8/2011 | Lin et al. |
| 2011/0218331 A1 | 9/2011 | Buffa et al. |
| 2011/0263724 A1 | 10/2011 | Gurtner et al. |
| 2012/0245323 A1 | 9/2012 | Buffa et al. |
| 2012/0264913 A1 | 10/2012 | Buffa et al. |
| 2012/0277416 A1 | 11/2012 | Carter et al. |
| 2012/0289478 A1 | 11/2012 | Rovati |
| 2013/0195791 A1* | 8/2013 | Berkland ............ A61K 39/385 424/78.27 |
| 2015/0320873 A1 | 11/2015 | Smejkalova et al. |

FOREIGN PATENT DOCUMENTS

| | | |
|---|---|---|
| CN | 101897976 A | 12/2010 |
| CN | 102154738 A | 8/2011 |
| CN | 103505736 A | 1/2014 |
| CZ | 2006605 A3 | 4/2008 |
| CZ | 20070299 A3 | 2/2009 |
| CZ | 301899 B6 | 7/2010 |
| CZ | 302503 B6 | 6/2011 |
| CZ | 302504 B6 | 6/2011 |
| CZ | 302856 B6 | 12/2011 |
| CZ | 302994 B6 | 2/2012 |
| CZ | 20101001 A3 | 2/2012 |
| CZ | 20120537 A3 | 3/2014 |
| CZ | 305153 B6 | 5/2015 |
| DE | 10331342 A1 | 2/2005 |
| EP | 0161887 A2 | 11/1985 |
| EP | 0216453 A2 | 4/1987 |
| EP | 0763754 A2 | 3/1997 |
| EP | 0554898 B1 | 5/1997 |
| EP | 1369441 A1 | 12/2003 |
| EP | 1454913 A1 | 9/2004 |
| EP | 1115433 B1 | 12/2004 |
| EP | 1538166 A1 | 6/2005 |
| EP | 1217008 B1 | 3/2006 |
| EP | 1826274 A1 | 8/2007 |
| EP | 1905456 A1 | 4/2008 |
| EP | 1607405 B1 | 5/2011 |
| EP | 2399940 A2 | 12/2011 |
| EP | 2522337 A2 | 11/2012 |
| JP | 62104579 A | 5/1987 |
| JP | 63044883 A | 11/1988 |
| JP | H0214019 A | 1/1990 |
| JP | 06025306 A | 2/1994 |
| JP | H0625306 A | 2/1994 |
| JP | 3308742 B2 | 7/2002 |
| JP | 2004507586 A | 3/2004 |
| JP | 2007262595 A | 10/2007 |
| JP | 3975267 B2 | 12/2007 |
| JP | 2008208480 A | 9/2008 |
| JP | 2008295885 A | 12/2008 |
| JP | 2010138276 A | 6/2010 |
| KR | 20070118730 A | 12/2007 |
| KR | 20080062092 A | 7/2008 |
| NL | 9700003 A | 7/1997 |
| WO | 199311803 A1 | 6/1993 |
| WO | 199627615 A1 | 9/1996 |
| WO | 199808876 A1 | 3/1998 |
| WO | 199901143 A1 | 1/1999 |
| WO | 199957158 A1 | 11/1999 |
| WO | 0063470 A1 | 10/2000 |
| WO | 0134657 A1 | 5/2001 |
| WO | 0218448 A2 | 3/2002 |
| WO | 0218450 A1 | 3/2002 |
| WO | 0232913 A1 | 4/2002 |
| WO | 0248197 A1 | 6/2002 |
| WO | 02057210 A1 | 7/2002 |
| WO | 2005028632 A2 | 3/2005 |
| WO | 2005092390 A2 | 10/2005 |
| WO | 2005092929 A1 | 10/2005 |
| WO | 2006010066 A2 | 1/2006 |
| WO | 2006026104 A2 | 3/2006 |
| WO | 2006056204 A1 | 6/2006 |
| WO | 2007003905 A1 | 1/2007 |
| WO | 2007006403 A2 | 1/2007 |
| WO | 2007009728 A2 | 1/2007 |
| WO | 2007033677 A1 | 3/2007 |
| WO | 2007101243 A1 | 9/2007 |
| WO | 2008014787 A1 | 2/2008 |
| WO | 2008031525 A1 | 3/2008 |
| WO | 2008077172 A2 | 7/2008 |
| WO | 2008115799 A1 | 9/2008 |
| WO | 2009037566 A2 | 3/2009 |
| WO | 2009050389 A2 | 4/2009 |

(56) References Cited

FOREIGN PATENT DOCUMENTS

| WO | 2009108100 A1 | 9/2009 |
|---|---|---|
| WO | 2009148405 A1 | 12/2009 |
| WO | 2010018324 A1 | 2/2010 |
| WO | 2010051783 A1 | 5/2010 |
| WO | 2010061005 A1 | 6/2010 |
| WO | 2010095049 A1 | 8/2010 |
| WO | 2010095052 A2 | 8/2010 |
| WO | 2010095056 A2 | 8/2010 |
| WO | 2010105582 A1 | 9/2010 |
| WO | 2010130810 A1 | 11/2010 |
| WO | 2010138074 A1 | 12/2010 |
| WO | 2011014432 A1 | 2/2011 |
| WO | 2011028031 A2 | 3/2011 |
| WO | 2011059325 A2 | 5/2011 |
| WO | 2011059326 A2 | 5/2011 |
| WO | 2011069474 A2 | 6/2011 |
| WO | 2011069475 A2 | 6/2011 |
| WO | 2012089179 A1 | 7/2012 |
| WO | 2012146218 A1 | 11/2012 |
| WO | 2013056312 A1 | 4/2013 |
| WO | 2013159757 A1 | 10/2013 |
| WO | 2014023272 A1 | 2/2014 |
| WO | 2014082608 A1 | 6/2014 |
| WO | 2014082609 A1 | 6/2014 |
| WO | 2014082611 A1 | 6/2014 |

OTHER PUBLICATIONS

Juhlin, L., "Hyaluronan in skin," Journal of Internal Medicine (1997) 242:61-66.
Kalyanaraman, B. et al., "Peroxidatic oxidation of catecholamines. A kinetic electron spin resonance investigation using the spin stabilization approach" Journal of Biological Chemistry (1984) 259(12)7584-7589.
Katritzky, A.R. et al., "Cycloaddition Reactions of Heteroaromatic Six-Membered Rings," Chem. Rev. (1989) 89:827-861.
Kawaguchi, Y. et al., "The relation between the adsorption behavior at the interface and the conformational changes in hyaluronates partially modified with various acyl chains," Carbohydrate Polymers (1995) 26:149-154.
Kedar, U. et al., "Advances in polymeric micelles for drug delivery and tumor targeting," Nanomedicine: Nanotechnology, Biology, and Medicine (2010) 6(6):714-729.
Kim, B. et al., "Complexation Phenomena in pH-Responsive Copolymer Networks with Pendent Saccarides," Macromol. (2002) 35:9545-9550.
Kim, T.G. et al., "Controlled Release of Paclitaxel from Heparinized Metal Stent Fabricated by Layer-by-Layer Assembly of Polylysine and Hyaluronic Acid-g-Poly(lactic-co-glycolic acid) Micelles Encapsulating Paclitaxel," Biomacromolecules (2009) 10(6):1532-1539.
Korsmeyer, R.W. et al., "Mechanisms of solute release from porous hydrophilic polymers," International Journal of Pharmaceutics (1983) 15:25-35.
Kumar, A. et al., "Development of hyaluronic acid-Fe2O3 hybrid magnetic nanoparticles for targeted delivery of peptides," Nanomedicine: Nanotechnology, Biology and Medicine, Elsevier, NL (2007) 3(2)132-137.
Kilo, J.W., "Practical Aspects of Hyaluronan Based Medical Products," 2006, CRC Press, Taylor & Francis Group, pp. 60-61.
Lapcik, L. Jr. et al., Chemicke Listy vol. 85, 1991, pp. 281-298.
Laurent, S. et al., "Magnetic fluid hyperthennia: Focus on superparamagnetic iron oxide nanoparticles," Advances in Colloid and Interface Science (2011) 166:8-23.
Leach, J.B. et al., "Characterization of protein release from photocrosslinkable hyaluronic acid-polyethylene glycol hydrogel tissue engineering scaffolds," Biomaterials (2005) 26:125-135.
Leach, J.B. et al., "Photocrosslinked Hyaluronic Acid Hydrogels: Natural, Biodegradable Tissue Engineering Scaffolds," Biotechnol Bioeng. (2003) 82:578-589.

Lee, Dong-Eun et al., "Amphiphilic hyaluronic acid-based nanoparticles for tumor-specific optical/MR dual imaging," Journal of Materials Chemistry (2012) 22(1)10444-10447.
Lee, F. et al., "An injectable enzymatically crosslinked hyaluronic acid-tyramine hydrogel system with independent tuning of mechanical strength and gelation rate," Soft Matter (2008) 4:880-887.
Lee, F. et al., "An injectable hyaluronic acid-tyramine hydrogel system for protein delivery," Journal of Controlled Release (2009) 134:186-193.
Lee, K.Y. et al., "Electrospinning of polysaccharides for regenerative medicine," Advanced Drug Delivery Reviews (2009) 61:1020-1032.
Lee, S.A. et al., "Spectroscopic studies of the physical properties of hyaluronate films: the origin of the phase transition," Carbohydrate Polymers (1995) 28:61-67.
Lee, Yuhan et al., "Bioinspired Surface Immobilization of Hyaluronic Acid on Monodisperse Magnetite Nanocrystals for Targeted Cancer Imaging," Advanced Materials (2008) 20:4154-4157.
Li, J.et al., "Electrospinning of Hyaluronic Acid (HA) and HA/Gelatin Blends," Macromolecular Rapid Communications (2006) 27:114-120.
Li, J. et al., "Redox-sensitive micelles self-assembled from amphiphilic hyaluronic acid-deoxycholic acid conjugates for targeted intracellular delivery of paclitaxel," Biomaterials (2012) 33(7):2310-2320.
Li, M. et al., Comparison of Two Ultrasmall Superparamagnetic Iron Oxides on Cytotoxicity and MR Imaging of Tumors, Theranostics (2012) 2(1):76-85.
Linhardt, R.J. et al., "Polysaccharide lyases," Applied Biochemistry and Biotechnology (1986) 12:135-176.
Linhartova, B., Nanovlakna na bazi hyaluronanu, Bakalarska prace, Vysoke uceni technicke v Brne, 2008 (English language Abstract on p. 3).
Liu, Yanchun et al., "Biocompatibility and stability of disulfide-crosslinked hyaluronan films," Biomaterials vol. 26, No. 23, 2005, pp. 4737-4746.
Liu, Yanhua et al., "Dual targeting folate-conjugated hyaluronic acid polymeric micelles for paclitaxel delivery," International Journal of Pharmaceutics (2011) 421(1):160-169.
Luo, Y. et al., "Novel amphoteric pH-sensitive hydrogels derived from ethylenediaminetetraacetic dianhydride, butanediamine and amino-terminated poly(ethylene glycol): Design, synthesis and swelling behavior," European Polymer Journal (2011) 47:40-47.
Maeda, H., "The Enhanced Permeability and Retention (EPR) Effect in Tumor Vasculature: The Key Role of Tumor-Selective Macromolecular Drug Targeting," Advances in Enzyme Regulation (2001) 41(1):189-207.
Malkoch, M. et al., "Synthesis of well-defined hydrogel networks using Click chemistry," Chem. Commun. (2006) 2774-2776.
Marega, R. et al., "Hyaluronan-Carbon Nanotube Derivatives: Synthesis, Conjugation with Model Drugs, and DOSY NMR Characterization," Eur. J. Org. Chem. (2011) 28:5617-5625.
Matsushima, R. et al., "Photoreactions of Alkylated 2-Pyridones," J. Chem. Soc. Perkin Trans. 2 (1985) 1445-1448.
Mayol, L. et al., "Amphiphilic hyaluronic acid derivatives toward the design of micelles for the sustained delivery of hydrophobic drugs," Carbohydrate Polymers (2014) 102:110-116.
Mazzone, S.B., "Fluorescent styryl dyes FM 1-43 and FM2-10 are muscarinic receptor antagonists: intravital visualization of receptor occupancy," The Journal of Physiology (2006) 575(1):23-35.
McIntyre, J.E., "The Chemistry of Fibres," Studies in Chemistry No. 6, 1971, p. 15.
McTaggart, L.E. et al., "Assessment of polysaccharide gels as drug delivery vehicles," Int. J. Pharm. 1993, vol. 100, pp. 199-206.
Merriam Webster Online Dictionary, obtained online at: http://www.merriam-webster.com/cgi-bin/dictionary?book=Dictionary&va=derivative, downloaded on Jul. 5, 2008.
Milas, M. et al., "Characterization and Properties of Hyaluronic Acid (Hyaluronan)," Polysaccharides: Structural Diversity and Functional Versatility, by S. Dumitriu 1998, Marcel Dekker Inc., pp. 535-549.

(56) References Cited

OTHER PUBLICATIONS

Miller, R.J. et al., Chemistry and Biology of Hyaluronan : Medicinal Uses of Modified Hyaluronate. Elsevier Ltd. 2004. 505-528.
Nevell, T.P. et al., "Cellulose Chemistry and its Applications," 1985, John Wiley & Sons, pp. 455-479.
Office Action in U.S. Appl. No. 13/512,484, dated May 11, 2016, 8 pgs.
Office Action in U.S. Appl. No. 13/512,484, dated Oct. 1, 2015, 8 pgs.
Office Action in U.S. Appl. No. 13/512,484, dated Sep. 11, 2014, 8 pgs.
Office Action in U.S. Appl. No. 13/514,759, dated Jul. 30, 2015, 12 pgs.
Office Action in U.S. Appl. No. 13/514,759, dated Sep. 24, 2014, 10 pgs.
Office Action in U.S. Appl. No. 13/977,181, dated Jan. 22, 2016, 8 pgs.
Office Action in U.S. Appl. No. 14/113,527, dated Feb. 12, 2016, 11 pgs.
Office Action in U.S. Appl. No. 14/113,527, dated Sep. 8, 2016, 10 pgs.
Office Action in U.S. Appl. No. 14/420,012, dated Jun. 16, 2016, 6 pgs.
Akkara, J. A.. et al., "Synthesis and characterization of polymers produced by horseradish peroxidase in dioxane," Journal of Polymer Science Part A: Polymer Chemistry (1991) 29(11):1561-1574.
Aldrich, Chem Files Synthetic Methods Oxidation, May 2005, vol. 5, No. 1 pp. 1-11 (English language translation included).
Angelin, M. et al., "Direct, Mild, and Selective Synthesis of Unprotected Dialdo-Glycosides," European Journal of Organic Chemistry (2006):4323-4326.
Armstrong, D.C. et al., "Culture Conditions Affect the Molecular Weight Properties of Hyaluronic Acid Produced by *Streptococcus zooepidemicus*," Appl. Environ. Microbiol. (1997) 63(7):2759-2764.
Atkins, E.D.T. et al., "The Conformation of the Mucopolysaccharides," J. Biochem vol. 128, 1972, pp. 1255-1263.
Atkins, E.D.T. et al., "The Molecular Structure of Hyaluronic Acid," Biochemical Journal (1971) 125(4):92.
Author unknown, "Readily Accessible 12-I-51Oxidant for the Conversion of Primary and Secondary Alcohols to Aldehydes and Ketones," Journal of Organic Chemistry (1983) 84:4155-4156 (English language on pp. 2-3 of document).
Author unknown, Encyclopedia of Cellulose, Asakura Publishing Co., Ltd., Nov. 10, 2000, pp. 155-156 (English language translation included).
Bakke, M. et al., "Identification, characterization, and molecular cloning of a novel hyaluronidase, a member of glycosyl hydrolase family 16, from *Penicillium* spp.," FEBS Letters (2011) 585(1):115-120.
Banerii, S. et al., "Structures of the Cd44-hyaluronan complex provide insight into a fundamental carboxyhydrate-protein interaction," Nature structural and molecular biology (2007) 14:234-239.
Benedetti, L. et al., Biocompatibility and biodegradation of different hyaluronan derivatives (Hyaff) implanted-in rats. Biomaterials 1993, 14 (15), 1154-1160.
Bezakova, Z. et al., "Effect of microwave irradiation on the molecular and structural properties of hyaluronan," Carbohydrate Polymers (2008) 73(4):640-646.
Boyer, I.J., "Toxicity of dibutyltin, tributyltin and other organotin compounds to humans and to experimental animals," Toxicology (1989) 55(3), 253-298.
Buffa, R. et al., "Branched hyaluronic acid, synthesis, analysis and biological properties," Journal of Tissue Engineering and Regenerative Medicine (2014) 8(1):321.
Buffa, R. et al., "New method of immobilization of hyaluronic acid oligomers," Journal of Tissue Engineering and Regenerative Medicine (2014) 8(1):321-322.
Burdick, J.A. et al., "Controlled Degradation and Mechanical Behavior of Photopolymerized Hyaluronic Acid Networks," Biomacromolecules (2005) 6:386-391.
Burdick, J.A. et al., "Hyaluronic Acid Hydrogels for Biomedical Applications," Adv. Mater. (2011) 23:H41-H56.
Burke, J., Solubility Parameters: Theory and Application, The Book and Paper Group Annual, vol. Three, 1984, 62 pgs.
Burner, U. et al., "Transient-state and steady-state kinetics of the oxidation of aliphatic and aromatic thiols by horseradish peroxidase," FEBS Letters (1997) 411(2-3):269-274.
Chen, L. et al., "Synthesis and pH sensitivity of carboxymethyl chitosan-based polyampholyte hydrogel for protein carrier matrices," Biomaterials (2004) 25:3725-3732.
Cornwell, M.J. et al., "A One-Step Synthesis of Cyclodextrin Monoaldehydes," Tetrahedron Letters (1995) 36 (46):8371-8374.
Crescenzi, V. et al., "Novel Hydrogels via Click Chemistry: Synthesis and Potential Biomedical Applications," Biomacromolecules (2007) 8:1844-1850.
Czech Official Action in Czech Patent Application No. PV 2008-705, dated Oct. 23, 2009, 2 pgs.
Czech Official Action in Czech Patent Application No. PV 2009-835, dated Aug. 2010, 2 pgs.
Czech Official Action in Czech Patent Application No. PV 2009-836, dated Aug. 6, 2010, 2 pgs.
Czech Search Report in Czech Patent Application No. PV 2010-1001, dated Sep. 27, 2011, 1 pg.
Czech Search Report in Czech Patent Application No. PV 2011-241, dated Nov. 30, 2011, 1 pg.
Czech Search Report in Czech Patent Application No. PV 2012-136, dated Sep. 18, 2012, 3 pgs.
Czech Search Report in Czech Patent Application No. PV 2012-282, dated Jan. 30, 2013, 1 pg.
Czech Search Report in Czech Patent Application No. PV 2012-306, dated Feb. 11, 2013, 1 pg.
Czech Search Report in Czech Patent Application No. PV 2012-664, dated May 24, 2013, 3 pgs.
Czech Search Report in Czech Patent Application No. PV 2012-842, dated Aug. 19, 2013, 3 pgs.
Czech Search Report in Czech Patent Application No. PV 2012-843, dated Aug. 20, 2013, 1 pg.
Darr, A. et al., "Synthesis and characterization of tyramine-based hyaluronan hydrogels," Journal of Materials Science: Materials in Medicine (2009) 20(1), 33-44.
Dilling, W.L. et al., "Organic Photochemistry. XII. The Photodimerization and Photoisomerization of 2-Pyridone and Its Monochloro Derivatives," Mol. Photochem. (1973) 5(4):371-409.
Ding, B. et al., "TEMPO-mediated selective oxidation of substituted polysaccharides-an efficient approach for the determination of the degree of substitution at C-6," Carbohydrate Research (2008) 343(18)3112-3116.
Donati, A. et al., "Solution Structure of Hyaluronic Acid Oligomers by Experimental and Theoretical NMR, and Molecular Dynamics Simulation," Biopolymers (2001) 59:434-445.
Duncan, R. et al., "Nanomedicine(s) under the Microscope," Molecular Pharmaceutics (2011) 8(6)2101-2141.
Dunford, H. B. et al., "Kinetics of the oxidation of p-aminobenzoic acid catalyzed by horseradish peroxidase compounds I and II," J Biol Chem 1975, 250(8), 2920-32.
Eenschooten, C. et al., "Preparation and structural characterisation of novel and versatile amphiphilic octenyl succinic anhydride-modified hyaluronic acid derivatives," Carbohydrate Polymers (2010) 79(3):597-605.
Ei-Dakdouki, M.H. et al., "Development of drug loaded nanoparticles for tumor targeting. Part 1: synthesis, characterization, and biological evaluation in 2D cell cultures," Nanoscale (2013) 5(9):3895-3903.
Ei-Dakdouki, M.H. et al., "Development of Multifunctional Hyaluronan-Coated Nanoparticles for Imaging and Drug Delivery to Cancer Cells," Biomacromolecules (2012) 13(4):1144-1151.
Ei-Sherbiny, I.M. et al., "Poly(ethylene glycol)-carboxymethyl chitosan-based pH-responsive hydrogels: photo-induced synthesis, characterization, swelling, and in vitro evaluation as potential drug carriers," Carbohydrate Research (2010) 3452004-2012.

(56) References Cited

OTHER PUBLICATIONS

Elander, R.P., "Industrial production of β-lactam antibiotics," Applied Microbiology and Biotechnology (2003) 51:385-392.
European First Official Action in European Patent Application No. 10812840.6-1306, dated Jul. 2, 2013, 4 pgs.
European Second Official Action in European Patent Application No. 10812840.6-1306, dated Sep. 24, 2014, 5 pgs.
Feng, Qian et al., "Self-Assembly Behaviour of Hyaluronic Acid on Mica by Atomic Force Microscopy," vol. 20, No. 1, 2004, pp. 146-148 and 152 (English language Abstract p. 152).
Ferrero, C. et al., "Fronts movement as a useful tool for hydrophilic matrix release mechanism elucidation," International Journal of Pharmaceutics (2000) 202:21-28.
Ferruti, P. et al., "Novel Poly(amido-amine)-Based Hydrogels as Scaffolds for Tissue Engineering," Macromol. Biosci. (2005) 5:613-622.
Fleige, E. et al., "Stimuli-responsive polymeric nanocarriers for the controlled transport of active compounds: Concepts and applications," Advanced Drug Delivery Reviews (2012) 64(9):866-884.
Office Action in U.S. Appl. No. 15/038,078, dated Nov. 3, 2017, 10 pgs.
International Search Report in International Patent Application No. PCT/CZ2016/000027, dated Jun. 27, 2016, 3 pgs.
Office Action in U.S. Appl. No. 15/322,776, dated Sep. 12, 2017, 23 pgs.
Written Opinion in International Patent Application No. PCT/CZ2016/000027, dated Jun. 27, 2016, 6 pgs.
Office Action in U.S. Appl. No. 14/647,626, dated Jun. 16, 2017, 14 pgs.
Office Action in U.S. Appl. No. 14/647,649, dated May 31, 2017, 11 pgs.
Veitch, N.C., "Horseradish peroxidase: a modern view of a classic enzyme," Phytochemistry (2004) 65:249-259.
Wang, J. et al., "Polymeric Micelles for Delivery of Poorly Soluble Drugs: Preparation and Anticancer Activity In Vitro of Paclitaxel Incorporated into Mixed Micelles Based on Poly(ethylene Glycol)-Lipid Conjugate and Positively Charged Lipids," Journal of Drug Targeting (2005) 13(1):73-80.
Wang, X. et al., "Formation of water-resistant hyaluronic acid nanofibers by blowing-assisted electro-spinning and non-toxic post treatments," Polymer (2005) 46:4853-4867.
Weng, L. et al., "In vitro and in vivo suppression of cellular activity by guanidinoethyl disulfied released from hydrogel microspheres composed of partially oxidized hyaluronan and gelatin," Biomaterials, Aug. 3, 2008, vol. 29, pp. 1149-4156.
Weng, L. et al., "Self-crosslinkable hydrogels composed of partially oxidized hyaluronan and gelatin: in vitro and in vivo responses," Journal of Biomedical Materials Research Part A, Aug. 9, 2007, pp. 352-365.
Wermuth, C.G., "Similarity in drugs: reflections on analogue design," Drug Discovery Today (2006) 11(7/8):348-354.
Won, K. et al., "Horseradish Peroxidase-Catalyzed Polymerization of Cardanol in the Presence of Redox Mediators," Biomacromolecules (2003) 5(1), 1-4.
Wondraczek, H. et al., "Synthesis of highly functionalized dextran alkyl carbonates showing nanosphere formation," Carbohydrate Polymers (2011) 83:1112-1118.
Written Opinion in International Patent Application No. PCT/CZ2009/000131, dated Apr. 9, 2010, 3 pgs.
Written Opinion in International Patent Application No. PC/CZ2010/000030, dated Sep. 1, 2010, 4 pgs.
Written Opinion in International Patent Application No. PCT/CZ2010/000128, dated Jun. 9, 2011, 4 pgs.
Written Opinion in International Patent Application No. PCT/CZ2010/000129, dated Jun. 15, 2011, 4 pgs.
Written Opinion in International Patent Application No. PCT/CZ2011/000126, dated Apr. 12, 2012, 4 pgs.
Written Opinion in International Patent Application No. PCT/CZ2012/000035, dated Aug. 28, 2012, 4 pgs.
Written Opinion in International Patent Application No. PCT/CZ2013/000023, dated Aug. 9, 2013, 3 pgs.
Written Opinion in International Patent Application No. PCT/CZ2013/000057, dated Jul. 24, 2013, 4 pgs.
Written Opinion in International Patent Application No. PCT/CZ2013/000063, dated Apr. 23, 2015, 9 pgs.
Written Opinion in International Patent Application No. PCT/CZ2013/000091, dated Oct. 31, 2013, 4 pgs.
Written Opinion in International Patent Application No. PCT/CZ2013/000116, dated Jan. 28, 2014, 5 pgs.
Written Opinion in International Patent Application No. PCT/CZ2013/000155, dated Feb. 19, 2014, 6 pgs.
Written Opinion in International Patent Application No. PCT/CZ2013/000156, dated Apr. 4, 2014, 7 pgs.
Written Opinion in International Patent Application No. PCT/CZ2013/000157, dated Mar. 19, 2014, 6 pgs.
Written Opinion in International Patent Application No. PCT/CZ2013/000158, dated Mar. 19, 2014, 7 pgs.
Written Opinion in International Patent Application No. PCT/CZ2014/000138, dated May 4, 2015, 5 pgs.
Written Opinion in International Patent Application No. PCT/CZ2015/000018, dated Jul. 22, 2015, 8 pgs.
Written Opinion in International Patent Application No. PCT/CZ2015/000068, dated Jan. 8, 2016, 6 pgs.
Xu, Y.-P. et al. "Kinetics of Phenolic Polymerization Catalyzed by Peroxidase in Organic Media," Biotechnology and Bioengineering (1995) 47(1):117-119.
Yamane, Shintaro et al., "Feasibility of chitosan-based hyaluronic acid hybrid biomaterial for a novel scaffold in cartilage tissue engineering," Biomaterials (2005) 26(6);611-619.
Yao, F. et al., "A Novel Amphoteric, pH-Sensitive, Biodegradable Poly[chitosan-g-(L-lactic-co-citric) acid] Hydrogel," Journal of Applied Polymer Science (2003) 89:3850-3854.
Yeom, J. et al., "Effect of Cross-Linking Reagents for Hyaluronic Acid Hydrogel Dermal Fillers on Tissue Augmentation and Regeneration," Bioconjugate Chemistry (2010) 21(2):240-247.
Zeng, J. et al., "Photo-Induced Solid-State Crosslinking of Electrspun Poly(vinyl alcohol) Fibers," Macromolecular Rapid Communications (2005) 26:1557-1562.
Zhong, S.P. et al., "Biodegradation of hyaluronic acid derivatives by hyalurondiase," Biomaterials (1994) 15 (5):359-365.
Funakoshi, T. et al., "Novel chitosan-based hyaluronan hybrid polymer fibers as a scaffold in ligament tissue engineering," Journal of Biomedical Materials Reasearch, Part A (2005) 74A(3):338-346.
Ghan, R. et al., "Enzyme-Catalyzed Polymerization of Phenols within Polyelectrolyte Microcapsules," Macromolecules (2004) 37(12), 4519-4524.
Gibby, W.A., "Cross-Linked DTPA Polysaccharides for Magnetic Resonance Imaging, Synthesis and Relaxation Properties," Invest. Radiol. 1989, vol. 24, pp. 302-309.
Gilabert, M.A. et al., "Differential substrate behaviour of phenol and aniline derivatives during oxidation by horseradish peroxidase: kinetic evidence for a two-step mechanism," Biochim. Biophys. Acta. (2004) 1699:235-243.
Gilabert, M.A. et al., "Kinetic characterization of phenol and aniline derivates as substrates of peroxidase," Biol. Chem. (2004) 385(9):795-800.
Gilabert, M.A. et al., "Stereospecificity of horseradish peroxidase," Biol. Chem. (2004) 385:1177-1184.
Godula, K. et al., "Synthesis of Glycopolymers for Microarray Applications via Ligation of Reducing Sugars to a Poly (acryloyl hydrazide) Scaffold," J. Am. Chem. Soc. (2010) 132:9963-9965.
Gong, J. et al., "Polymeric micelles drug delivery system in oncology," Journal of Controlled Release (2012) 159 (3):312-323.
Guillaumie, F. et al., "Comparative studies of various hyaluronic acids produced by microbial fermentation for potential topical ophthalmic applications," Journal of Biomedical Materials Research Part A (2009) 1421-1430.
Gupta, P. et al., "Hydrogels: from controlled release to pH-responsive drug delivery," Drug Discovery Today (2002) 7 (10):569-579.

(56) References Cited

OTHER PUBLICATIONS

Hasegawa, T. et al., "'Click chemistry' on polysaccharides: a convenient, general, and monitorable approach to develop (1-3)-β-D-glucans with various functional appendages," Carbohydrate Research (2006) 341:35-40.
Hewson, W. D. et al., "Oxidation of p-cresol by horseradish peroxidase compound I," J Biol Chem 1976, 251 (19), 6036-42.
Hewson, W. D. et al., "Stoichiometry of the reaction between horseradish peroxidase and p-cresol," J Biol Chem 1976, 251(19), 6043-52.
Higashimura, H. et al., Oxidative Polymerization. John Wiley & Sons, Inc. Olefin Fibers (2002) 10:740-764.
Hocek, M., "Tvorba C-C A C-X Vazeb Cross-Coupling Reakcemi Katalyzovanymi Komplexy Prechodnych Kovu," Chem. Listy (2003) 97:1145-1150.
Hoffman, A.S., "'Intelligent' Polymers in Medicine and Biotechnology," Artificial Organs (1995) 19(5):458-467.
Hofmann, H et al. "Conformational Changes of Hyaluronic Acid in Acid Medium," Albrecht Von Graefe's Archive for Clinical and Experimental Opthamology vol. 198, No. 1, 1976, pp. 95-100.
Holten, K.B. et al., "Appropriate Prescribing of Oral Beta-Lactam Antibiotics," American Family Physician (2000) 62 (3):611-620.
Huang, G. et al., "Superparamagnetic Iron Oxide Nanoparticles: Amplifying ROS Stress to Improve Anticancer Drug Efficacy.," Theranostics (2013) 3(2):116-126.
Huerta-Angeles, G. et al., "Synthesis of highly substituted amide hyaluronan derivatives with tailored degree of substitution and their crosslinking via click chemistry," Carbohydrate Polymers (2011) 84:1293-1300.
Huh, K.M. et al., "Hydrotropic polymer micelle system for delivery of paclitaxel," Journal of Controlled Release (2005) 101:59-68.
Hynes, W.L. et al., "Hyaluronidases of Gram-positive bacteria," FEMS Microbiology Letters (2000) 183:201-207.
Inanaga, J. et al., "A Rapid Esterification by Means of Mixed Anhydride and Its Application to Large-ring Lactonization," Bulletin of the Chemical Society of Japan (1979) 52(7):1989-1993.
International Search Report in International Patent Application No. PCT/CZ2009/000131, dated Apr. 9, 2010, 3 pgs.
International Search Report in International Patent Application No. PCT/CZ2010/000030, dated Sep. 1, 2010, 3 pgs.
International Search Report in International Patent Application No. PCT/CZ2010/000128, dated Jun. 9, 2011, 3 pgs.
International Search Report in International Patent Application No. PCT/CZ2010/000129, dated Jun. 15, 2011, 3 pgs.
International Search Report in International Patent Application No. PCT/CZ2011/000126, dated Apr. 12, 2012, 3 pgs.
International Search Report in International Patent Application No. PCT/CZ2012/000035, dated Aug. 28, 2012, 3 pgs.
International Search Report in International Patent Application No. PCT/CZ2013/000023, dated Aug. 9, 2013, 3 pgs.
International Search Report in International Patent Application No. PCT/CZ2013/000057, dated Jul. 24, 2013, 4 pgs.
International Search Report in International Patent Application No. PCT/CZ2013/000063, dated Apr. 23, 2015, 7 pgs.
International Search Report in International Patent Application No. PCT/CZ2013/000091, dated Oct. 31, 2013, 3 pgs.
International Search Report in International Patent Application No. PCT/CZ2013/000116, dated Jan. 28, 2014, 4 pgs.
International Search Report in International Patent Application No. PCT/CZ2013/000155, dated Feb. 19, 2014, 4 pgs.
International Search Report in International Patent Application No. PCT/CZ2013/000156, dated Apr. 4, 2014, 5 pgs.
International Search Report in International Patent Application No. PCT/CZ2013/000157, dated Mar. 19, 2014, 3 pgs.
International Search Report in International Patent Application No. PCT/CZ2013/000158, dated Mar. 19, 2014, 3 pgs.
International Search Report in International Patent Application No. PCT/CZ2014/000138, dated May 4, 2015, 4 pgs.
International Search Report in International Patent Application No. PCT/CZ2015/000018, dated Jul. 22, 2015, 5 pgs.
International Search Report in International Patent Application No. PCT/CZ2015/000068, dated Jan. 8, 2016, 4 pgs.
Jacoboni, I., "Hyaluronic Acid by Atomic Force Microscopy," Journal of Structural Biology vol. 126, 1999, pp. 52-58.
Jahn, M. et al., "The reaction of hyaluronic acid and its monomers glucuronic acid and N-acetylglucosamine, with reactive oxygen species," Carbohydrate Research, 1999, vol. 321, pp. 228-234.
Japanese Official Action (English language translation) in Japanese Patent Application No. 2012-542355, dated Oct. 17, 2014.
Japanese Official Action (English language translation) in Japanese Patent Application No. 2014-506754, dated Jan. 22, 2015, 2 pgs.
Japanese Official Action (including English language translation) in Japanese Patent Application No. 2012-542356, dated Oct. 3, 2014, 8 pgs.
Jia, X.Q. et al., "Synthesis and Characterization of in Situ Cross-Linkable Hyaluronic Acid-Based Hydrogels with Potential Application for Vocal Fold Regeneration," Macromolecules (2004) 37:3239-3248.
Jiang, B. et al., "Study on TEMPO-mediated selective oxidation of hyaluronan and the effects of salt on the reaction kinetics," Carbohydrate Research, Pergamon, GB (2000) 327(4)455-461.
Jin, R. et al., "Enzyme-mediated fast in situ formation of hydrogels from dextran-tyramine conjugates," Biomaterials (2007) 28(18):2791-2800.
Job, D. et al., "Substituent effect on the oxidation of phenols and aromatic amines by horseradish peroxidase compound I," Eur J Biochem 1976, 66 (3), 607-14.
Office Action in U.S. Appl. No. 14/430,731, dated May 19, 2016, 12 pgs.
Office Action in U.S. Appl. No. 14/647,185, dated Sep. 28, 2016, 5 pgs.
Office Action in U.S. Appl. No. 14/647,626, dated Feb. 17, 2017, 12 pgs.
Office Action in U.S. Appl. No. 14/647,626, dated Jul. 28, 2016, 35 pgs.
Oh, E.J. et al., "Target specific and long-acting delivery of protein, peptide, and nucleotide therapeutics using hyaluronic acid derivatives," J. Controlled Release vol. 141, 2010, pp. 2-12.
Pal, K. et al., "Biopolymers in Controlled-Release Delivery Systems," Modern Biopolymer Science (2009) 519-557.
Park, Y.D. et al., "Photopolymerized hyaluronic acid-based hydrogels and interpenetrating networks," Biomaterials (2003) 24:893-900.
Patel, P.K. et al., "Kinetic studies on the oxidation of phenols by the horseradish peroxidase compound II," Biochim Biophys Acta (1997) 1339(1):79-87.
Piluso, S. et al., "Hyaluronic acid-based hydrogels crosslinked by copper-catalyzed azide-alkyne cycloaddition with tailorable mechanical properties," International Journal of Artificial Organs (2011) 34:192-197, Abstract.
Prestwich, G.D., "Biomaterials from Chemically-Modified Hyaluronan," internet article, Feb. 26, 2001, 17 pgs.
Prestwich, G.D., "Hyaluronic acid-based clinical biomaterials derived for cell and molecule delivery in regenerative medicine," Journal of Controlled Release (2011) 155:193-199.
Qiu, Y. et al., "Environment-sensitive hydrogels for drug delivery," Advanced Drug Delivery Reviews (2001) 53:321-339.
Rao, K.V.R. et al., "Influence of Molecular Size and Water Solubility of the Solute on its Release from Swelling and Erosion Controlled Polymeric Matrices," Journal of Controlled Release (1990) 12:133-141.
Remy, H., Anorganicka chemie II., Sntl Praha 1971, pp. 306-321.
Ritger, P.L. et al., "A Simple Equation for Description of Solute Release I. Fickian and Non-Fickian Release from Non-Swellable Devices in the Form of Slabs, Spheres, Cylinders or Discs," Journal of Controlled Release (1987) 5:23-36.
Ritger, P.L. et al., "A Simple Equation for Description of Solute Release II. Fickian and Anomalous Release from Swellable Devices," Journal of Controlled Release (1987) 5:37-42.
Rostovtsev, V.V. et al., "A Stepwise Huisgen Cycloaddition Process: Copper(I)-Catalyzed Regioselective 'Ligation' of Azides and Terminal Alkynes," Angew. Chem. Int. Ed. (2002) 41(14):2596-2599.

(56) References Cited

OTHER PUBLICATIONS

Ruoslahti, E. et al., "Targeting of drugs and nanoparticles to tumors," The Journal of Cell Biology (2010) 188 6):759-768.
Rupprecht, A., "Wet Spinning of Hyaluronic Acid. Preparation of Oriented Samples," Acta. Chem. Scand. vol. B33, No. 10, 1979, pp. 779-780.
Sahiner, N. et al., "Fabrication and characterization of cross-linkable hydrogel particles based on hyaluronic acid: potential application in volcal fold regeneration", Journal of Biomaterials Science, Polymer Edition, vol. 19, Issue 2, pp. 223-243.
Schante, C.E. et al., "Chemical modifications of hyaluronic acid for the synthesis of derivatives for a broad range of biomedical applications," Carbohydrate Polymers (2011) 85:469-489.
Scott, J.E. et al., "Periodate Oxidation of Acid Polysaccharides", Histochemie, Apr. 26, 1969, vol. 19, pp. 155-161.
Scott, J.E. et al., "Secondary and tertiary structures of hyaluronan in aqueous solution, investigated by rotary shadowing—electron microscopy and computer simulation," J. Biochem vol. 274, 1991, pp. 699-705.
Sedova, P. et al., "Preparation of hyaluronan polyaldehyde—a precursor of biopolymer conjugates," Carbohydrate Research (2013) 371:8-15.
Seidlits, S.K. et al., "The effects of hyaluronic acid hydrogels with tunable mechanical properties on neural progenitor cell differentiation" Biomaterials (2010) 31:3930-3940.
Shang, J. et al., "Chitosan-based electroactive hydrogel," Polymer (2008) 49:5520-5525.
Sheehan, J.K. et al., "X-ray Diffraction Studies on the Connective Tissue Polysaccharides," J. Mol. Biol. (1975) 91:153-163.
Shen, Y. et al., "Synthesis and characterization of low molecular weight hyaluronic acid-based cationic micelles for efficient siRNA delivery," Carbohydrate Polymers (2009) 77(1):95-104.
Shen, Yi et al., "Synthesis, Characterization, Antibacterial and Antifungal Evaluation of Novel Monosaccharide Esters," Molecules (2012) 17(7):8661-8673.
Shimizu, M. et al., "Studies on hyaluronidase, chondroitin sulphatase, proteinase and phospholipase secreted by Candida species," MYCOSES (1996) 39:161-167.
Shutava, T. et al., "Microcapsule Modification with Peroxidase-Catalyzed Phenol Polymerization," Biomacromolecules (2004) 5(3):914-921.
Sieburth, S.M. et al., "Fusicoccin Ring System by [4+4} Cycloaddition. 2. A Model Study," Tetrahedron Letters (1999) 40:4007-4010.
Sieburth, S.M. et al., "The [4+4] Cycloaddition and its Strategic Application in Natural Product Synthesis," Tetrahedron (1996) 52(18):6251-6282.
Slaughter, B.V. et al., "Hydrogels in Regenerative Medicine," Advanced Materials (2009) 21(32-33)3307-3329.
Slezingrova, K. et al., "Synteza a charakterizace palmitoyl hyaluronanu," Chemicke Listy (2012) 106:554-567.
Smeds, K.A. et al., "Photocrosslinkable polysaccharides for in situ hydrogel formation," J. Biomed. Mater. Res. (2001) 54:115-121.
Smejkalova, D. et al., "Structural and conformational differences of acylated hyaluronan modified in protic and aprotic solvent system," Carbohydrate Polymers (2012) 87(2):1460-1466.
Staskus, P.W. et al., "Double-Stranded Structure for Hyaluronic Acid in Ethanol-Aqueous Solution As Revealed by Circular Dichroism of Oligomers," Biochemistry vol. 27, No. 5, 1988, pp. 1528-1534.
Svanovsky, E. et al., "The effect of molecular weight on the biodistribution of hyaluronic acid radiolabeled with 111-In after intravenous administration to rats," Eur. J. Drug Metab. Ph. 2008, vol. 33, No. 3, pp. 149-157.
Tan, H. et al., "Injectable in situ forming biodegradable chitosan-hyaluronic acid based hydrogels for cartilage tissue engineering," Biomaterials (2009) 30(13):2499-2506.
Tankam, P.F. et al., "Alkynyl polysaccharides: synthesis of propargyl potato starch followed by subsequent derivatizations," Carbohydrate Research (2007) 342:2049-2060.
Tao, Y. et al., "Core cross-linked hyaluronan—styrylpyridinium micelles as a novel carrier for paclitaxel," Carbohydrate Polymers (2012) 88(1):118-124.
Testa, G. et al., "Influence of dialkyne structure on the properties of new click-gels based on hyaluronic acid," International Journal of Pharmaceutics (2009) 378:86-92.
Thakar, D. et al., "A quartz crystal microbalance method to study the terminal functionalization of glycosaminoglycans," Chemical Communications (2014) 50(96):15148-15151.
Til, H.P. et al., "Acute and Subacute Toxicity of Tyramine, Spennidine, Spennine, Putrescine and Cadaverine in Rats," Food and Chemical Toxicology (1997) 35(3-4):337-348.
Tonelli, A.E., "Effects of crosslink density and length on the number of intramolecular crosslinks (defects) introduced into a rubbery network," Polymer (1974) 15(4):194-196.
Tornoe, C. et al., "Peptidotriazoles on Solid Phase: [1,2,3]-Triazoles by Regiospecific Copper(I)-Catalyzed 1,3-Dipolar Cycloadditions of Terminal Alkynes to Azides," J. Org. Chem. (2002) 67:3057-3064.
Um, I.C. et al., "Electro-Spinning and Electro-Blowing of Hyaluronic Acid, " Biomacromolecules (2004) 5:1428-1436.
Uyama, H. et al., "Enzymatic Synthesis of Polyphenols," Current Organic Chemistry (2003) 7:1387-1397.
Van Bommel, K.J.C. et al., "Responsive Cyclohexane-Based Low-Molecular-Weight Hydrogelators with Modular Architecture," Angew. Chem. Int. Ed. (2004) 1663-1667.
Office Action in U.S. Appl. No. 14/395,575, dated Jul. 6, 2017, 9 pgs.
Office Action in U.S. Appl. No. 15/322,776, dated Jul. 14, 2017, 11 pgs.

* cited by examiner

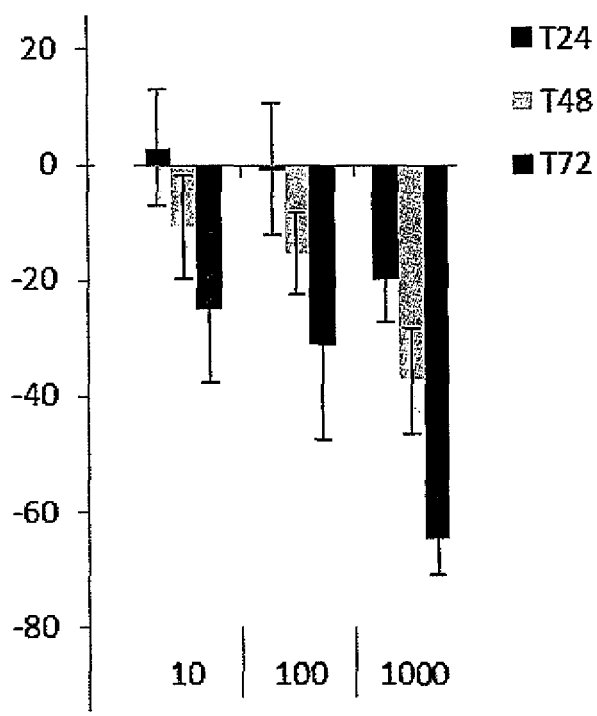

CONJUGATES OF OLIGOMER OF HYALURONIC ACID OR OF A SALT THEREOF, METHOD OF PREPARATION THEREOF AND USE THEREOF

FIELD OF THE ART

The invention relates to conjugates of hyaluronic acid or a salt thereof, method of preparation thereof and use thereof.

By means of such conjugates, it is possible to immobilize oligomers of hyaluronic acid with the possibility of releasing them in their original, native form.

STATE OF THE ART

Hyaluronic acid is a glycosaminoglycan composed of two repeating saccharidic cycles of β-(1,3)-D-glucuronic acid and β-(1,4)-N-acetyl-D-glucosamine.

Scheme 1: hyaluronic acid

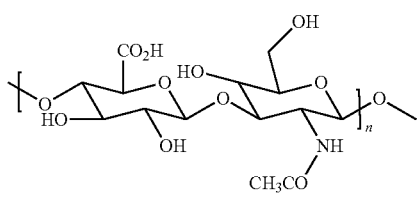

It is characterized by a high molecular weight of $5 \cdot 10^4$ to $5 \cdot 10^6$ g·mol$^{-1}$ which depends on the method of isolation thereof and the initial material. This very hydrophilic polysaccharide is water-soluble in the form of a salt within the whole pH range. It forms a part of connective tissues, skin, synovial fluid of joints, it plays an important role in a number of biological processes such as hydration, proteoglycan organisation, cell differentiation, proliferation and angiogenesis.

Bonding of HA Oligomers

As mentioned above, the native hyaluronic acid is a linear polysaccharide which is degraded in the organism quite fast. The first convincing attempts of preparation of hyaluronan having a branched structure were described in 2008 by Toemmeraase K. (WO 2008/014787). It concerns bonding of the amino group of deacetylated hyaluronan having a higher molecular weight with the ending anomeric center of hyaluronan oligomer by means of reductive amination. The authors of another patent document, Hacker M., Saraf A., Mikos A. G., WO 2008/115799, proceeded in a similar way in case of bonding the ending anomeric center of HA oligomer to polyethylene imine. In order to ensure strong bonding, reductive amination is used which converts amino glycosides to hydrolytically extremely stable secondary amines. The reaction takes place in a slightly basic environment and at an elevated temperature and sodium cyanoborohydride is used as the reducing agent. The resulting conjugates were used for encapsulation of DNA or mesenchymal stem cells, wherein only a hexamer is mentioned as the hyaluronan oligomer. Another possibility was disclosed in the article Eur. J. Org. Chem. 2011, 5617-25. Here, an amino group is generated in the position 6 of the glucosamine part of the HA oligomer, which amino group then reacts at mild conditions with NHS esters of carboxylic acids bound to carbon nanotubes. Bonding of the ending anomeric center of hyaluronan having a lower molecular weight by means of a diamino or polyamino linker using the reductive amination is disclosed by Xu (WO 2007/101243). The resulting substrates were used for encapsulation of active substances. Another possibility was disclosed by Carter (US 2012/0277416), where phospholipids were bound to the ending anomeric center of HA oligomer. In the first step, a derivative of an oligomer having an amine in the position 1 was prepared by means of reductive amination, then it was conjugated with an active carboxylic group of a phospholipid. The resulting conjugates exhibited a wide range of biological activities. A similar procedure of bonding to a HA oligomer having an amino group at the reduced anomeric end was published by Siiskonen in 2013, where a mark 2-aminoacridon was bound. Said conjugate was used for studying the biodistribution of hyaluronan fragments in cytosol.

A drawback of the above mentioned methods is the fact that they allow the formation of conjugates of HA oligomers or polymers which do not allow their further release in the native form. The cause thereof is the fact that all up-till-now known methods of bonding amines to the ending anomeric center are associated with the reduction, i.e. with an irreversible modification of the ending cycle which remains permanently open and does not allow the reverse release of the oligomer in the native form. The situation is illustrated by the following Scheme 1:

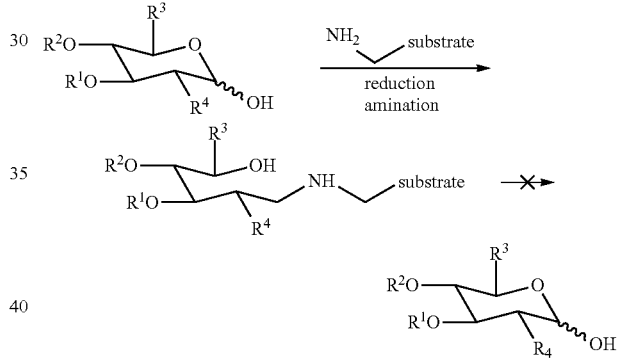

Subject-Matter of the Invention

The above mentioned drawbacks are overcome by the conjugates of HA oligomers of the general formulae I, II, III or IV according to this invention which do allow such reverse release of HA oligomers in the native form.

The subject-matter of the invention is the conjugate of an oligomer of hyaluronic acid or of a salt thereof according to any of the general I, II, III or IV, (I)

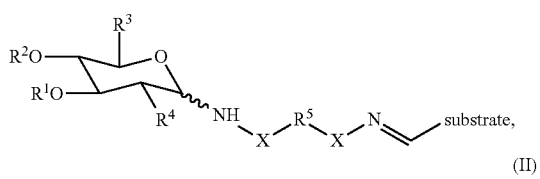

(II)

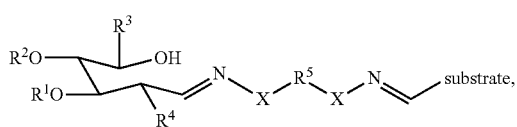

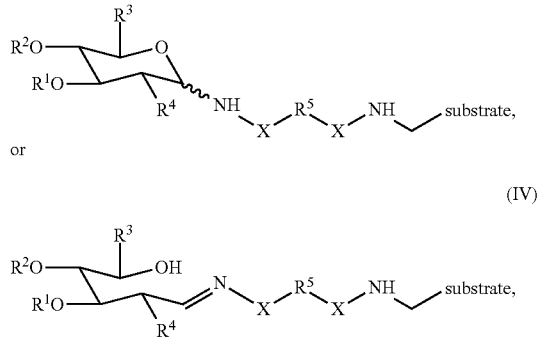

where $R^3$ is $COOR^6$ or $CH_2OH$, $R^4$ is OH or $NHCOCH_3$, $R^6$ is $H^+$ or is selected from the group comprising any of alkali metal ions or alkaline-earth metal ions, preferably $Na^+$, $Mg^{2+}$ or $Li^+$;

$R^5$ is selected from the group comprising $C_1$-$C_{30}$ alkyl, $C_1$-$C_{30}$ alkylaryl, or $C_1$-$C_{30}$ alkyl heteroaryl optionally comprising one or more identical or different heteroatoms selected from the group comprising N, O, S X is O or NH group;

in case that $R^3$ is $COOR^6$, then $R^4$ is OH, $R^1$ is H, $R^2$ is a residue of hyaluronic acid oligomer;

in case that $R^3$ is $CH_2OH$, then $R^4$ is $NHCOCH_3$, $R^2$ is OH, $R^1$ is a residue of hyaluronic acid oligomer;

substrate is a polysaccharide, preferably it is selected from the group comprising hyaluronic acid or a pharmaceutically acceptable salt thereof, having the molecular weight within the range $10^4$ to $10^6$ g·mol$^{-1}$, preferably $10^5$ g·mol$^{-1}$.

The structure of the resulting conjugates depends to a great extent on the character of the substitute X. If X is an oxygen bridge —O—, an imino form is significantly present. If X is a nitrogen bridge —NH—, the dominant form is an amino having the beta configuration.

The residue of hyaluronic acid oligomer in the conjugate according to this invention has 1 to 17 saccharidic cycles, wherein the saccharidic cycle is selected from the group consisting of β-(1,3)-D-glucuronic acid and β-(1,4)-N-acetyl-D-glucosamine.

According to another embodiment, the conjugates of hyaluronic acid oligomer of the general formulae I and II defined above may be prepared by the method of the invention, the subject-matter of which is that in the first step an oligomer of hyaluronic acid reacts on its ending anomeric center in the position 1 with an excess of a diamino linker of the general formula $H_2N$—X—$R^5$—X—$NH_2$, where $R^5$ is selected from the group comprising $C_1$-$C_{30}$ alkyl, $C_1$-$C_{30}$ alkylaryl, or $C_1$-$C_{30}$ alkylheteroaryl which optionally comprises one or more identical or different heteroatoms selected from the group comprising N, O, S, and X is O or NH group; in a slightly acid environment at the pH within the range 3 to 6.99, preferably at pH within the range 3 to 6, more preferably 5 to 6, whereafter the conjugates of hyaluronic acid oligomer-diamino linker of the general formulae V and VI are isolated where the substitutes $R^1$ to $R^6$ are as defined above.

The proceeding of the first step of the reaction is illustrated by Scheme 2 below.

Scheme 2:

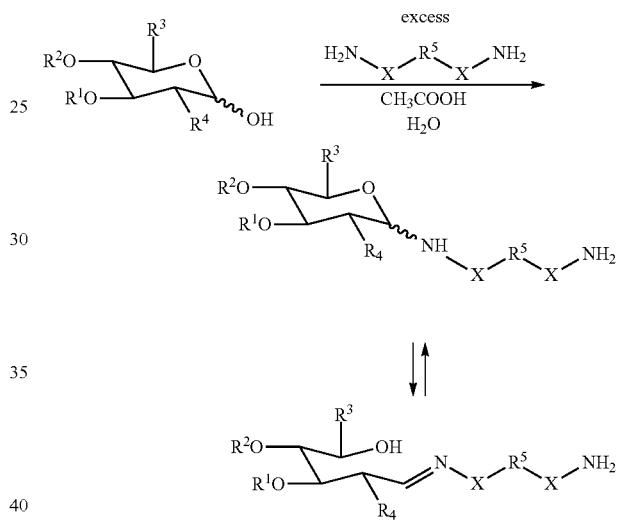

The reaction takes place at an excess of the diamino linker which statistically eliminates significantly the modification at both ends of the linker.

It was surprisingly found out that this reaction proceeds only in the presence of a certain amount of a weak acid and water. If the conditions were neutral or basic, no successful reaction was observed. Ha strong acid such as HCl or $H_2SO_4$ was present, degradation of HA oligomers occurred.

The slightly acidic environment having the pH within the range 3 to 6.99 is achieved by an addition of a carboxylic acid to the reaction medium, preferably acetic acid, propanoic acid or lactic acid, more preferably acetic acid.

The amount of the acid is within the range of 5 to 30 equivalents, preferably within the range of 10 to 15 equivalents, with respect to the molar amount of the disaccharide of hyaluronic acid as a substrate.

Further, the amount of the diamino linker is within the range of 5 to 30 equivalents, preferably 10 equivalents, with respect to the molar amount of the disaccharide of hyaluronic acid as a substrate.

Further, the first step proceeds at the temperature of 10 to 40° C., preferably at the temperature of 20° C., for 24 to 150 hours, preferably 60 to 80 hours.

Thereafter, the second step of the reaction takes place, in which the conjugates of the hyaluronic acid oligomer-diamino linker of the general formulae V and VI, as defined above, are reacted with at least one aldehydic group of the substrate in water or in a mixture of water and a water-miscible organic solvent which is selected from the group comprising ethanol, isopropanol, methanol or dimethylsulfoxide.

Moreover, the second step is carried out at the temperature of 10 to 40° C. as well, preferably at 20° C., for 24 to 150 hours, preferably 60 to 80 hours.

According to another preferred embodiment of the method of the invention, conjugates of the oligomer of hyaluronic acid-diamino linker according to the general formula V and VI, as defined above, are reacted, according to the method and conditions as stated above, with at least one aldehydic group of the substrate in the presence of a reducing agent which is preferably selected from the group comprising cyano borohydride (NaBH$_3$CN) or picoline borane, to form conjugates of the general formulae III and IV, where the substrate is bound by a hydrolytically very strong bond.

The amount of the reducing agent is within the range of 0.1 to 5 equivalents, preferably 3 equivalents, with respect to the molar amount of the hyaluronic acid disaccharide.

Both above described possibilities of bonding the substrate by amination or reductive amination are shown in Scheme 3 linkage oligomer-linker, which has basically also the character of a reducing imine, has been observed.

Efforts of bonding the ending anomeric center of the HA oligomer with the conjugate substrate linker have not been successful even at higher temperatures when peeling cleavage of HA oligomers occurred

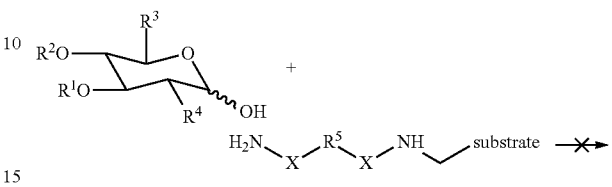

therefore, when preparing the final conjugate it is necessary to bind the bifunctional linker to the oligomer first.

From the above mentioned facts it follows that when preparing the conjugates according to the invention, it was necessary to find the reaction conditions which were finally found in a relatively narrow range (pH in a weak acid region, a careful reduction . . . ). The final conjugates of the general formulae I, II, III, IV allow, as compared to the solutions known so far, to release hyaluronan oligomers in their original native form, which is important in terms of their Scheme 3

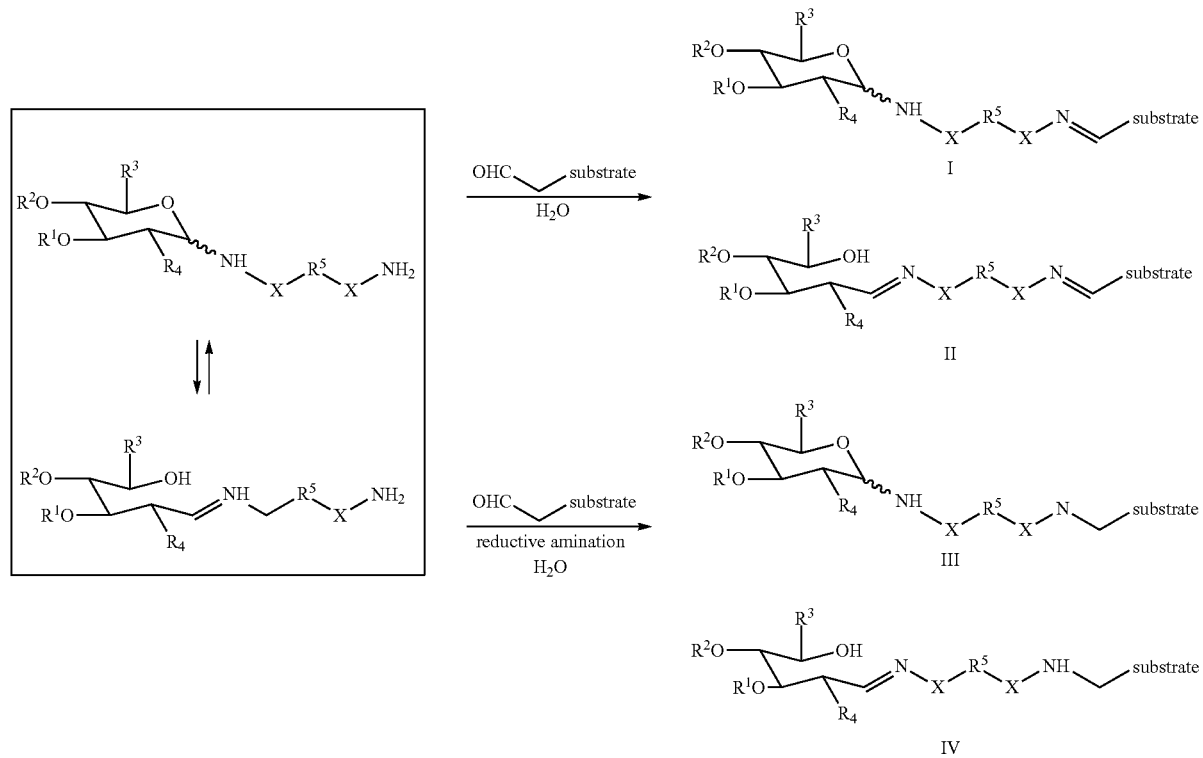

It is surprising that during the reductive amination where conjugates of the general formulae III and IV (see Scheme above) are formed, the reduction proceeds substantially only on the linkage substrate linker, which is due to the compromise conditions such as the reaction temperature, time, the amount of the reducing agent, and no reduction of the biological activity. The necessary condition is that the substrate contains aldehydic groups, which may be quite easily achieved by a chemical modification such as by oxidation in case of polysaccharides containing OH groups.

The realization of the solutions disclosed in this invention is not complicated technologically and does not require the use of expensive chemicals, solvents or isolation procedures.

As already described above, the conjugate according to this invention allows the release:

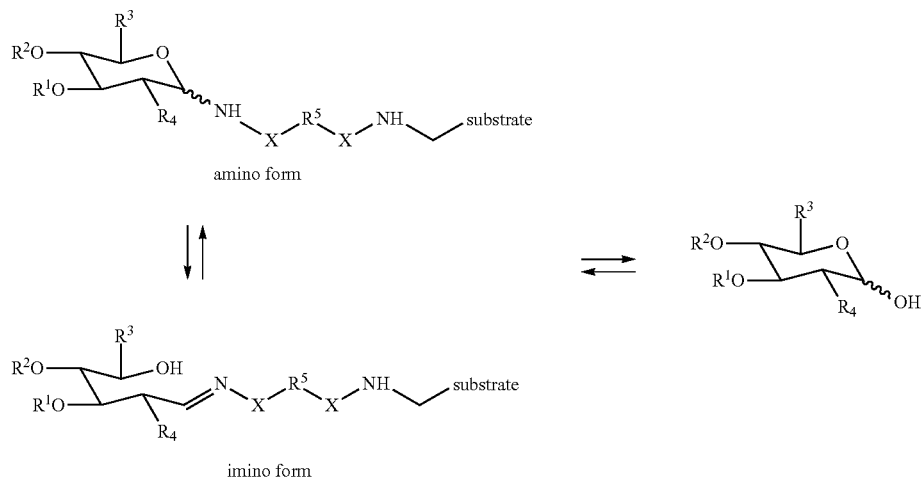

The possibility of the reversible immobilisation is very important in cases where it is necessary to maintain the original structure of oligomers for the sake of their biological activity or biocompatibility. It is known that some types of HA oligomers exhibit the biological activity for example to cancer cells. The prepared systems exhibited an enhanced biological activity against selected lines of cancer cells.

According to another embodiment of the invention the conjugates of the general formulae I to IV, as defined above, are preferably used as carriers of biologically active oligomers in pharmacy and biomedicine, or it is possible to use them for the preparation of materials having an anticancer effect.

The term "pharmaceutically acceptable salt", as used herein, means salts of HA conjugates according to the invention, which are safe and effective for an in vivo use and have the desired biological activity. The pharmaceutically acceptable salts include preferably ions of alkali metals or alkaline earth metals, more preferably $Na^+$, $K^+$, $Mg^+$ or $Li^+$.

The term "polysaccharide" means a polysaccharide, such as hyaluronic acid, a pharmaceutical salt thereof, starch, glycogen, cellulose etc., which contain at least one aldehydic group after the oxidation of their OH groups.

The term "conjugate" means a compound which is formed by bonding of two or more chemical compounds by means of a covalent bond. The conjugate according to this invention is formed by bonding a HA oligomer and a linker giving rise to a conjugate HA oligomer-linker and then by bonding thereof to a substrate, i.e. a polysaccharide, preferably hyaluronic acid, while forming the conjugate HA oligomer-linker-substrate.

The term "oligomer of hyaluronic acid" means an oligomer of hyaluronic acid containing alternately repeating saccharidic cycles β-(1,3)-D-glucuronic acid and β-(1,4)-N-acetyl-D-glucosamine. Preferably, the number of saccharidic cycles is 2 to 18.

The term "the residue of hyaluronic acid oligomer" means at least one saccharidic cycle of hyaluronic acid oligomer, which is β-(1,4)-N-acetyl-D-glucosamine or β-(1,3)-D-glucuronic acid.

In case that the ending saccharidic cycle bonded to the linker via its anomeric center is β-(1,3)-D-glucuronic acid, said one saccharidic cycle is β-(1,4)-N-acetyl-D-glucosamine.

In case that the ending saccharidic cycle bonded to the linker via its anomeric center is β-(1,4)-N-acetyl-D-glucosamine, said one saccharidic cycle is β-(1,3)-D-glucuronic acid.

In case that the residue of hyaluronic acid oligomer comprises more than one saccharidic cycle, the saccharidic cycles of β-(1,3)-D-glucuronic acid and fβ-(1,4)-N-acetyl-D-glucosamine are repeated alternately.

The term "excess" means an amount of diamino linker which is higher than one equivalent with respect to the molar amount of hyaluronic acid disaccharide as a substrate.

The term "is isolated" means that after finishing the reaction, the reaction mixture is neutralised and the precipitated reaction product is filtered off and dried.

BRIEF DESCRIPTION OF DRAWINGS

FIG. 1 shows the course of inhibition of the growth of the imortalized cancerogenic cells in percents of the non-affected control.

EXAMPLES

The term equivalent (eq) used herein relates to a disaccharide of hyaluronic acid, if not indicated otherwise. The percents are meant to be weight percents, if not indicated otherwise.

The molecular weight of the initial hyaluronic acid (source: CPN spol. s r.o., Dolni Dobrouč, CZ) is a weight average molecular weight within the range of $10^4$ to $10^6$ g·mol$^{-1}$ and was measured by SEC-MALLS.

Hyaluronic acid oligomers comprising 2 to 18 saccharidic cycles were prepared by an enzymatic degradation of the polymer having a higher molecular weight.

DS=degree of substitution=100%*(molar amount of the bonded substitute or modified disaccharide)/(molar amount of all disaccharides)

Example 1 Preparation of HA-Aldehyde Oxidated in the Position 6 of the Glucosamine Part Oxidation of Hyaluronic Acid An aqueous NaClO solution (0.5 eq) was gradually added to a one-percent aqueous solution of hyaluronan (1 g, 200 kDa), containing NaCl 1%, TEMPO (0.01 eq) and NaHCO$_3$ (5 eq.), under the nitrogen atmosphere. The mixture was stirred for 12 hours at the temperature of 0° C., then 0.1 g of ethanol was added and the mixture was stirred for another 1 hour. The resulting solution was then diluted by distilled water to 0.2% and was dialysed against the mixture (0.1% NaCl, 0.1% NaHCO$_3$) 3-times 5 liters (once a day) and against distilled water 7-times 5 liters (twice a day). Then the resulting solution was evaporated and analysed. DS 10% (determined from NMR)

$^1$H NMR (D$_2$O) δ 5.26 (s, 1H, polymer-CH(OH)$_2$)

HSQC (D$_2$O) cross signal 5.26 ppm ($^1$H)-90 ppm ($^{13}$C) (polymer-CH(OH)$_2$)

Example 2 Preparation of a Conjugate of Octasaccharide of HA (HA-8) with Dihydrazide Adipate HA octasacharide was dissolved in water in a concentration of 5%. Then dihydrazide adipate (6 equivalents) and acetic acid (15 equivalents) were added and the mixture was stirred at the temperature of 20° C. for 72 hours at pH 4. The resulting mixture was neutralised with NaHCO$_3$ and repeatedly precipitated by means of isopropyl alcohol. The final solid product was dried in vacuum.

$^1$H NMR (D$_2$O) δ 4.24 (d, J=9.7 Hz, 1H, —O—CH—NH— beta), no signal of the initial ending anomeric center (—O—CH—OH alpha)

Example 3 Preparation of a Conjugate of HA Trisaccharide (HA-3) with Dihydrazide Adipate HA trisaccharide (ending with glucuronic acid) was dissolved in water in the concentration of 7%. Then dihydrazide adipate (25 equivalents) and acetic acid (25 equivalents) were added and the mixture was stirred at the temperature of 10° C. for 150 hours at pH 6. The resulting mixture was neutralised by NaHCO$_3$ and repeatedly precipitated by means of isopropyl alcohol. The final solid product was dried in vacuum.

$^1$H NMR (D$_2$O) δ 4.11 (d, J=8.8 Hz, 1H, —O—CH—NH— beta), no signal of the initial ending anomeric center (—O—CH—OH alpha)

Example 4 Preparation of the Conjugate of HA Octadeca (HA-18) with Dihydrazide Adipate HA octadecasaccharide (ending with glucosamine) was dissolved in water in the concentration of 5%. Then dihydrazide adipate (15 equivalents) and acetic acid (20 equivalents) were added and the mixture was stirred at the temperature of 40° C. for 24 hours at pH 5. The resulting mixture was neutralised by NaHCO$_3$ and repeatedly precipitated by means of isopropyl alcohol. The final solid product was dried in vacuum.

$^1$H NMR (D$_2$O) δ 4.10 (d, J=8.7 Hz, 1H, —O—CH—NH— beta),

Example 5 Preparation of the Conjugate of HA Decasaccharide (HA-10) with O,O'-4,3-Propane Diylbishydroxyl Amine HA decasaccharide was dissolved in water in the concentration of 3%. Then O,O'-4,3-propane diylbishydroxyl amine (5 equivalents) and lactic acid (5 equivalents) were added and the mixture was stirred at the temperature of 20° C. for 100 hours at pH 6. The resulting mixture was neutralised by NaHCO$_3$ and repeatedly precipitated by means of isopropyl alcohol. The final solid product was dried in vacuum.

$^1$H NMR (D$_2$O) δ 7.53 (d, J=5.3 Hz, 1H, —O—CH=N—Z-isomer), δ 6.89 (d, 1H, —O—CH=N-E-isomer),

Example 6 Preparation of the Conjugate of HA Tetrasaccharide (HA-4) with Terephthaloyl Dihydrazide HA tetrasaccharide was dissolved in water in the concentration of 3%. Then terephthaloyl dihydrazide (5 equivalents) and propanoic acid (6 equivalents) were added and the mixture was stirred at the temperature of 20° C. for 100 hours at pH 6. The resulting mixture was neutralised by NaHCO$_3$ and repeatedly precipitated by means of isopropyl alcohol. The final solid product was dried in vacuum.

$^1$H NMR (D$_2$O) δ 4.12 (d, J=8.8 Hz, 1H, —O—CH—NH— beta),

Example 7 Bonding of the Conjugate HA-8 Dihydrazide Adipate (Example 2) to Hyaluronan Oxidised in the Position 6 to an Aldehyde (Example 1) by Reductive Amination 0.01 g of the conjugate prepared according to Example 2 were dissolved in water in the concentration of 2%. Then 0.01 g of the derivative of hyaluronic acid containing an aldehyde (molecular weight 6×10$^5$ g·mol$^{-1}$) and 5 equivalents of picoline borane were added. The mixture was stirred at the temperature of 20° C. for 24 hours. The resulting mixture was precipitated by means of isopropyl alcohol. The final solid product was dried in vacuum.

$^1$H NMR (D$_2$O) δ 2.85, 3.12 (m,m diastereotoic pair, 2H, NH—CH$_2$-polymer)

DOSY NMR (D$_2$O) δ 4.24 (d, J=9.7 Hz, 1H, —O—CH—NH— beta) has the same mobility as hyaluronic acid having a higher molecular weight and signals of diastereotopic hydrogens of 2.85 a 3.12.

Example 8 Bonding of the Conjugate HA-3 Dihydrazide Adipate (Example 3) to Hyaluronan Oxidised in the Position 6 to an Aldehyde (Example 1) by Reductive Amination 0.01 g of the conjugate prepared according to Example 3 were dissolved in water in the concentration of 2%. Then 0.01 g of the derivative of hyaluronic acid containing an aldehyde (molecular weight 2×10$^4$ g·mol$^{-1}$) and 0.3 equivalents of sodium cyano borohydride were added. The mixture was stirred at the temperature of 10° C. for 72 hours. The resulting mixture was precipitated by means of isopropyl alcohol. The final solid product was dried in vacuum.

$^1$H NMR (D$_2$O) δ 2.89, 3.04 (m,m diastereotopic pair, 21-1, NH—CH$_2$-polymer)

DOSY NMR (D$_2$O) δ 4.11 (d, J=8.8 Hz, 1H, —O—CH—NH— beta) has the same mobility as hyaluronic acid having a higher molecular weight and signals of diastereotopic hydrogens of 2.89 a 3.04.

Example 9 Bonding of the Conjugate HA-8 Dihydrazide Adipate (Example 2) to Hyaluronan Oxidised in the Position 6 to an Aldehyde (Example 1) without Reduction 0.1 g of the conjugate prepared according to Example 2 were dissolved in a mixture of water/DMSO in the ratio 1/1 in the concentration of 2%. Then 0.1 g of the derivative of hyaluronic acid containing an aldehyde (molecular weight $2 \times 10^4$ g·mol$^{-1}$) was added. The mixture was stirred at the temperature of 20° C. for 72 hours. The resulting mixture was precipitated by means of isopropyl alcohol. The final solid product was dried in vacuum.

$^1$H NMR (D$_2$O) δ 7.48 (m, 111, NCH-polymer)

DOSY NMR (D$_2$O) δ 4.24 (d, J=9.7 Hz, 1H, —O—CH—NH— beta) has the same mobility as hyaluronic acid having a higher molecular weight and the signal 7.48.

Example 10 Bonding of the Conjugate HA-18 Dihydrazide Adipate (Example 4) to Hyaluronan Oxidised in the Position 6 to an Aldehyde (Example 1) without Reduction 0.1 g of the conjugate prepared according to Example 4 were dissolved in water in the concentration of 2%. Then 0.1 g of the derivative of hyaluronic acid containing an aldehyde (molecular weight $2 \times 10^4$ g·mol$^{-1}$) was added. The mixture was stirred at the temperature of 10° C. for 100 hours. The resulting mixture was precipitated by means of isopropyl alcohol. The final solid product was dried in vacuum.

$^1$H NMR (D$_2$O) δ 7.47 (m, 114, NCH-polymer)

DOSY NMR (D$_2$O) δ 4.25 (d, J=9.7 Hz, 1H, —O—CH—NH— beta) has the same mobility as hyaluronic acid having a higher molecular weight and the signal 7.47.

Example 11 Bonding of the Conjugate HA-10-O,O"-1,3-Propane Diylbishydroxyl-Amine (Example 5) to Hyaluronan Oxidised in the Position 6 to an Aldehyde (Example 1) without Reduction 0.01 g of the conjugate prepared according to Example 5 were dissolved in water in the concentration of 2%. Then 0.01 g of the derivative of hyaluronic acid containing an aldehyde (molecular weight $2 \times 10^4$ g·mol$^{-1}$) was added. The mixture was stirred at the temperature of 20° C. for 48 h. The resulting mixture was precipitated by means of isopropyl alcohol. The final solid product was dried in vacuum.

DOSY NMR (D$_2$O) δ 7.53 (d, J=5.3 Hz, 1H, —O—CH═N—Z-isomer), δ 6.89 (d, J=6.0 Hz, 1H, —O—CH═N-E-isomer) have the same mobility as hyaluronic acid having a higher molecular weight.

Example 12 Biological Testing of the Conjugate Prepared According to Example 8

Determination of the viability of the line A2058 after the treatment with the conjugate prepared according to Example 8:

The cell line cultured at standard conditions (medium DMEM with 10% FBS, 37° C., 5% CO$_2$) was seeded into 4 96-wells culture panels in the density of 5000 cells per a well and incubated in 200.1 of the medium for 24 hours. Thereafter, the culture medium was exchanged for a fresh medium containing the conjugate (Example 8) in concentrations 1000, 100 and 10 μg/ml. The medium for the control cells was exchanged for a fresh one without the conjugate. Immediately after the treatment, the cell viability was measured in the first panel by means of the MTT method. In brief, 20 μl of the MTT solution (5 mg/ml) were added to the cells and together they were incubated for 2.5 hours in dark at 37° C. After the incubation, the culture medium was sucked off and the cell monolayer was lysed by a mixture of DMSO and isopopanol (1:1) with 10% Triton X-100. The resulting colour in individual wells of the panel was measured by means of a plate spectrophotometer (absorbance at 570 nm with the correction at 690 nm). This measurement was repeated at the other panels as well every 24 hours. The final viability was calculated as the ratio of the absorbance of the sample in a given time and in time T0.

A2058 is an immortalised cell line derived from the human melanoma, it is very invasive and for that reason, it is often used as a model of tumorigenesis and metastasizing.

The results of the inhibition of the cell growth in percents are shown in FIG. 1, where it is clear that the inhibition of the cell growth increases exponentially in time due to the influence of the conjugate according to the invention.

The invention claimed is:

1. A conjugate of an oligomer of hyaluronic acid or a salt thereof according to any of the general formulae I, II, III or IV,

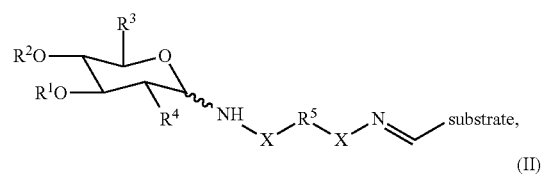

(I)

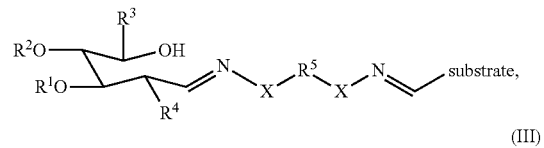

(II)

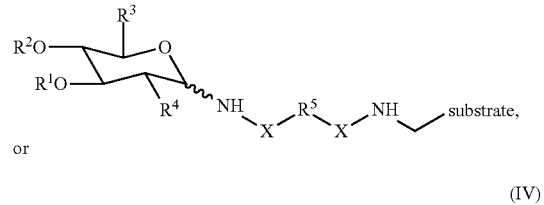

(III)

or

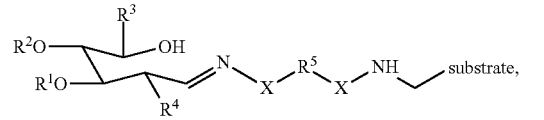

(IV)

where
  $R^3$ is COOR$^6$ or CH$_2$OH,
  $R^4$ is OH or NHCOCH$_3$,
  $R^6$ is H$^+$ or is selected from the group comprising any of alkali metal ions or alkaline earth metals;
  $R^5$ is selected from the group comprising C$_1$-C$_{30}$ alkyl, C$_1$-C$_{30}$ alkylaryl, or C$_1$-C$_{30}$ alkylheteroaryl optionally comprising one or more identical or different heteroatoms selected from the group comprising N, O, S;
  X is O or an NH group;
  in case that $R^3$ is COOR$^6$, $R^4$ is OH, $R^1$ is H, $R^2$ is a hyaluronic acid oligomer residue;
  in case that $R^3$ is CH$_2$OH, $R^4$ is NHCOCH$_3$, $R^2$ is H, $R^1$ is a hyaluronic acid oligomer residue; and
  substrate is a polysaccharide.

2. The conjugate according to claim 1, wherein the polysaccharide is selected from the group consisting of hyaluronic acid and a pharmaceutically acceptable salt thereof.

3. The conjugate according to claim 2, wherein the hyaluronic acid or the pharmaceutically acceptable salt thereof has the molecular weight within the range of $10^4$ to $10^6$ g·mol$^{-1}$.

4. The conjugate according to claim 1, wherein the hyaluronic acid oligomer residue comprises 1 to 17 saccharidic cycles selected from the group consisting of β-(1,3)-D-glucuronic acid and β-(1,4)-N-acetyl-D-glucosamine.

5. A method of preparation of conjugates of a hyaluronic acid oligomer, the method comprising reacting conjugates of hyaluronic acid oligomer-diaminolinker of the general formula V and VI

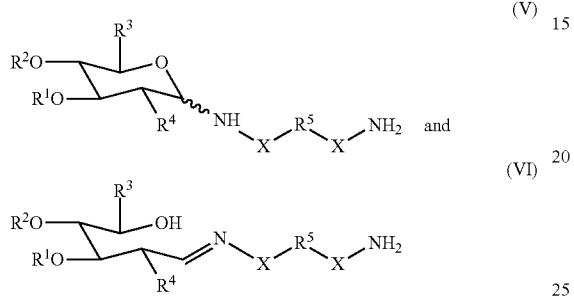

with an aldehydic group of a substrate in water or in a mixture of water and a water miscible solvent;
wherein:
R$^3$ is COOR$^6$ or CH$_2$OH,
R$^4$ is OH or NHCOCH$_3$,
R$^6$ is H or a pharmaceutically acceptable salt;
R$^5$ is selected from the group comprising C$_1$-C$_{30}$ alkyl, C$_1$-C$_{30}$ alkylaryl, or C$_1$-C$_{30}$ alkylheteroaryl optionally comprising one or more identical or different heteroatoms selected from the group comprising N, O, S;
X is O or an NH group;
in case that R$^3$ is COOR$^6$, then R$^4$ is OH, R$^1$ is H, R$^2$ is a hyaluronic acid oligomer residue;
in case that R$^3$ is —CH$_2$OH, then R$^4$ is NHCOCH$_3$, R$^2$ is H, R$^1$ is a hyaluronic acid oligomer residue; and
wherein the reaction forms conjugates of the hyaluronic acid oligomer according to the general formula I and II

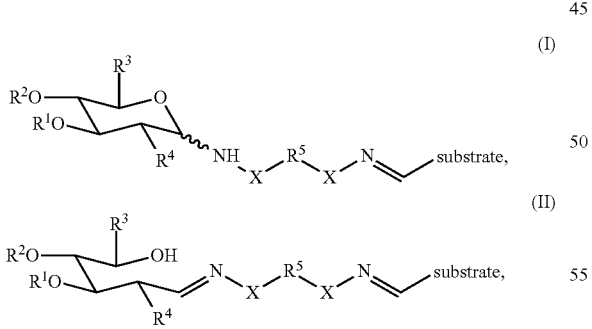

6. The method of preparation according to claim 5, wherein the hyaluronic acid oligomer residue comprises 1 to 17 saccharidic cycles selected from the group consisting of β-(1,3)-D-glucuronic acid and β-(1,4)-N-acetyl-D-glucosamine.

7. The method of preparation according to claim 5, wherein the substrate is a polysaccharide selected from the group consisting of hyaluronic acid and a pharmaceutically acceptable salt thereof.

8. The method according to claim 7, wherein the hyaluronic acid or the pharmaceutically acceptable salt thereof has the molecular weight within the range of $10^4$ to $10^6$ g·mol$^{-1}$.

9. The method of preparation according to claim 5, wherein it is carried out at a temperature of 10 to 40° C. for 24 to 150 hours.

10. The method of preparation according to claim 5, wherein the water miscible solvent is selected from the group of ethanol, isopropanol, methanol, and dimethylsulphoxide.

11. A method of preparation of conjugates of hyaluronic acid oligomer, comprising reacting conjugates of hyaluronic acid oligomer-diaminolinker of the general formula V and VI

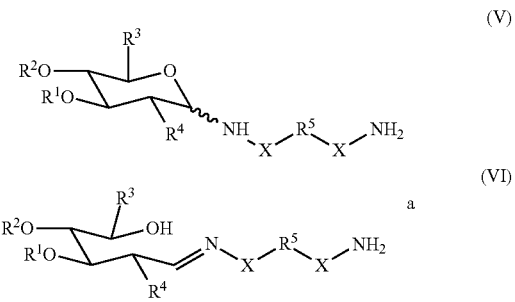

with at least one aldehydic group of a substrate in water or in a mixture of water and a water miscible solvent;
wherein:
R$^3$ is COOR$^6$ or CH$_2$OH,
R$^4$ is OH or NHCOCH$_3$,
R$^6$ is H or a pharmaceutically acceptable salt;
R$^5$ is selected from the group comprising C$_1$-C$_{30}$ alkyl, C$_1$-C$_{30}$ alkylaryl, or C$_1$-C$_{30}$ alkylheteroaryl optionally comprising one or more identical or different heteroatoms selected from the group comprising N, O, S;
X is O or an NH group;
in case that R$^3$ is COOR$^6$, then R$^4$ is OH, R$^1$ is H, R$^2$ is a hyaluronic acid oligomer residue;
in case that R$^3$ is —CH$_2$OH, then R$^4$ is NHCOCH$_3$, R$^2$ is H, R$^1$ is a hyaluronic acid oligomer residue;
further reacting the conjugates of hyaluronic acid oligomer-diaminolinker of the general formula V and VI with at least one aldehydic group of the substrate in the presence of a reducing agent;
to form conjugates of the hyaluronic acid oligomer according to the general formula III and IV.

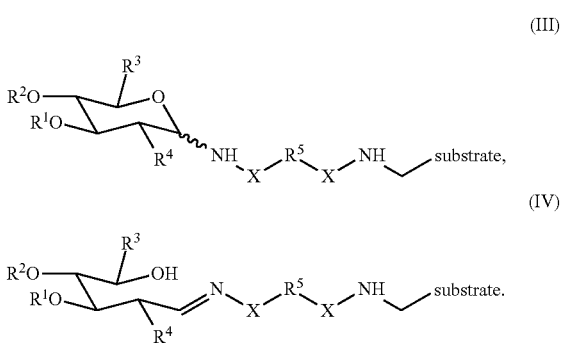

12. The method of preparation according to claim 11, wherein the reducing agent is selected from the group consisting of cyano borohydride and picoline borane.

13. The method of preparation according to claim 11 or claim 12, wherein the amount of the reducing agent is within the range 0.1 to 5 equivalents with respect to the molar amount of the hyaluronic acid disaccharide.

14. The method of preparation according to claim 5, wherein the conjugates of hyaluronic acid oligomer-diaminolinker of the general formula V and VI are prepared in such a way that the hyaluronic acid oligomer reacts at its ending anomeric center in the position 1 with an excess of diamino linker of the general formula $H_2N$—X—$R^5$—X—$NH_2$, where $R^5$ is selected from the group consisting of $C_1$-$C_{30}$ alkyl, $C_1$-$C_{30}$ alkylaryl, and or $C_1$-$C_{30}$ alkylheteroaryl optionally comprising one or more identical or different heteroatoms selected from the group consisting of N, O, and S, and X is O or an NH group; at pH within the range of 3 to 6.99, whereupon the conjugate of hyaluronic acid oligomer-diamino linker of the general formula V and VI is isolated.

15. The method of preparation according to claim 14, wherein the reaction is carried out at pH within the range 3 to 6.

16. The method of preparation according to claim 14 or claim 15, wherein the reaction is carried out in the presence of a carboxylic acid selected from the group consisting of acetic acid, propanoic acid, and lactic acid.

17. The method of preparation according to claim 16, wherein the amount of the carboxylic acid is within the range of 5 to 30 equivalents, with respect to the molar amount of the hyaluronic acid disaccharide.

18. The method of preparation according to claim 14, wherein the excess of the linker is within the range of 5 to 30 equivalents, with respect to the molar amount of the hyaluronic acid disaccharide as the substrate.

19. The method of preparation according to claim 14 wherein the reaction is carried out at the temperature 10 to 40° C. for 24 to 150 hours.

* * * * *

UNITED STATES PATENT AND TRADEMARK OFFICE
CERTIFICATE OF CORRECTION

PATENT NO. : 10,023,658 B2
APPLICATION NO. : 15/124827
DATED : July 17, 2018
INVENTOR(S) : Radovan Buffa et al.

It is certified that error appears in the above-identified patent and that said Letters Patent is hereby corrected as shown below:

On the Title Page

Under item (56), Other Publications Page 3, Column 1, Line 17, "Saccharides," should be -- Saccharides, --.

In the Specification

Column 2,
Line 51, "any of the general I, II, III or IV," should be -- any of the general formulae I, II, III or IV, --.

Column 3,
Line 25, "preferably $Na^+$, $Mg^{2+}$ or $Li^+$;" should be -- preferably $Na^+$, $K^+$, $Mg^{2+}$ or $Li^+$; --.

Column 5,
Line approx. 45 (bottom of box), "X" is missing from the formula drawing.

Column 6,
Line approx. 45 (formula III), "N" should be -- NH --.

Column 10,
Line 7, "Z-isomer), δ 6.89 (d, 1H, —O—CH=N-E-isomer)," should be -- Z-isomer), δ 6.89 (d, J=6.0Hz, 1H, —O—CH=N-E-isomer), --.
Line 47, "were dissolved" should be -- was dissolved --.
Line 55, "21-1, NH—$CH_2$-polymer)" should be -- 2H, —NH—$CH_2$-polymer) --.
Line 67, "were dissolved" should be -- was dissolved --.

Column 11,
Line 7, "(m, 111, NCH-polymer)" should be -- (m, 1H, —N=CH-polymer) --.
Line 18, "were dissolved" should be -- was dissolved --.
Line 24, "(m, 114, NCH-polymer)" should be -- (m, 1H, —N=CH-polymer) --.

Signed and Sealed this
Sixteenth Day of October, 2018

Andrei Iancu
*Director of the United States Patent and Trademark Office*

Line 36, "were dissolved" should be -- was dissolved --.

In the Claims

Column 14,
Line 9 (Claim 10), "group of" should be -- group consisting of --.
Line 51 (Claim 11), "general formula III and IV." should be -- general formulae III and IV: --.